United States Patent

Hassler et al.

[11] Patent Number: 5,846,543
[45] Date of Patent: Dec. 8, 1998

[54] BOVINE MASTITIS TREATMENT

[76] Inventors: Mark A. Hassler; Lisa M. Hassler, both of 102 Beaver Creek Rd., Fleetwood, Pa. 19522

[21] Appl. No.: 547,617

[22] Filed: Oct. 24, 1995

[51] Int. Cl.⁶ .......................... A01N 65/00; A61K 35/78; A61K 39/385; A61K 39/00
[52] U.S. Cl. ................................. 424/195.1; 424/184.1; 514/886; 514/887; 514/885
[58] Field of Search ............... 424/195.1, 184.1; 514/886, 887, 885

[56] References Cited

U.S. PATENT DOCUMENTS 5,061,491  10/1991  Deryabin .............................. 424/195.1
5,260,341  11/1993  Rajamannan ........................... 514/675
5,376,374  12/1994  Zelaya ................................. 424/195.1

OTHER PUBLICATIONS

Fang, W. et al., *Prev. Vet. Med.*, 15 (2–3):169–180, 1993.
Hu, S. et al., *J. Vet, Med. Ser. A*, 39 (8):593–99, 1992.

*Primary Examiner*—Nita Minnifield
*Attorney, Agent, or Firm*—Zachary T. Wobensmith, III

[57] ABSTRACT

Chemical compositions for the treatment of bovine mastitis which compositions are combinations of four components i.e.; Echinechea Goldenseal Supreme; Wild Ginseng Supreme; gelsemium, pokeroot, and aconite; and aloe vera juice, which form a dose which is injected into the mastitis affected portion of a cow's udder for a minimum of two doses per day for at least three days, which results in a cure for the mastitis.

23 Claims, No Drawings

BOVINE MASTITIS TREATMENT

BACKGROUND OF THE INVENTION

1. Field of the Invention

This invention relates to chemical compositions for treating bovine mastitis which compositions include Echinechea Goldenseal Supreme; Wild Ginseng Supreme; gelsemium, poke root, aconite; and aloe vera juice.

2. Description of the Prior Art

Dairy cows whose main purpose is to produce milk are subject to many disorders which can disrupt their milk production, and render the cow unfit to produce milk.

Dairy cows are expensive to own and maintain, and the standards for milk production are high.

It is essential that the cows are healthy and produce the maximum possible amount of milk.

A cow's udder is divided into four quarters and the milk produced from all the quarters must be free from disease or disease byproducts.

One of the disorders that affects cows is bovine mastitis. Bovine mastitis is inflammation of a cow's udder resulting from injury, or bruising, or more commonly from bacterial infection. Bovine mastitis is a major source of loss to the dairy industry both through direct damage to the cow and loss of milk production.

The treatment of choice for mastitis has been the administration of various antibiotics into the cow's udder.

The use of antibiotics is not entirely satisfactory as the antibiotics can carry over into the milk obtained from the cow which is undesirable, and the antibiotics may require long term treatment which is costly in terms of lost milk production and cost of the antibiotic. In addition, the administration of antibiotics in a significant number of cows does not result in a cure of the mastitis with the result that the cows are sent to slaughter.

The administration of the chemical compositions described herein has resulted in a complete cure of bovine mastitis for all the cows with which they have been used and without any undesirable carry over into the cow's milk.

SUMMARY OF THE INVENTION

The present invention is directed to chemical compositions for the treatment of bovine mastitis, which compositions contain Echinechea Goldenseal Supreme; Wild Ginseng Supreme; gelsemium, poke root, aconite; and aloe vera juice which are combined to form a dose that is injected directly into the affected cow's udder.

The principal object of the invention is to provide compositions for bovine mastitis treatment.

A further object of the invention is to provide compositions as aforesaid which are safe and practical to use.

A further object of the invention is to provide compositions as aforesaid which are highly effective in treating bovine mastitis in a short time period.

A further object of the invention is to provide compositions as aforesaid which do not produce any undesirable byproducts which can carry over into the cow's milk.

A further object of the invention is to provide compositions as aforesaid which are inexpensive.

Other objects and advantageous feature of the invention will be apparent from the description and claims.

It should, of course, be understood that the description is merely illustrative and that various modifications and changes can be made in the compositions disclosed without departing from the spirit of the invention.

DESCRIPTION OF THE PREFERRED EMBODIMENTS

When referring to the preferred embodiments, certain terminology will be utilized for the sake of clarity. Use of such terminology is intended to encompass not only the described embodiment, but also technical equivalents which operate and function in substantially the same way to bring about the same result.

The described compositions for treatment of bovine mastitis are formed of four components in liquid form, in various concentrations which are combined to form a twelve milliliter dose. The compositions all contain an aloe vera juice component at full strength which contains 99.7% aloe vera, and small amounts of potassium sorbate, sodium benzoate and ascorbic acid. The aloe vera juice is available from ALOE FARMS, Box 125, Los Fresnos, Tex. 78566.

The second component is Echinechea Goldenseal Supreme available from GHIA HERBS, INC., 12 Lancaster County Road, Harvard, Mass. 01451. Echinechea Goldenseal Supreme contains Echinechea Angustifolia root Echinechea Purpurea root, flowerhead seed Fresh Goldenseal Root (*Hydrastis Canadensis*)

Fresh Oregon Grape root (*Berbens Aquafolium*)

Fresh Barberry Root Bark (Berberis app.) and

Fresh St. Johnswort Flower buds (*Hypericum Perforatum Porpolis* Extract.

This component also contains grain alcohol in a range of 45 to 55%, with the fresh herb strength in a 1 to 1 ratio.

The third component is Wild Ginseng Supreme, available from GHIA HERBS INC., 12 Lancaster County Road, Harvard, Mass. 01451.

The Wild Ginseng Supreme contains

Wild American Ginseng (*Panax quinquifolium*) and

Wild Russian Siberian Ginseng (*Eleutherococcus Senticosus*)

This component also contains grain alcohol in a range of 30–35%, with a fresh herb strength in a ratio of 1 to 1.5.

The fourth component is a combination of gelsemium, pokeroot and aconite in equal parts.

The gelsemium is

Fresh Gelsemium root (*Gelsemium sempervirens*) with a fresh herb strength, in a ratio of 1 to 2.5 (1 gm. fresh root for every 2.5 cc extract)

The gelsemium is available from GHIA HERBS, INC., Harvard, Mass.

The pokeroot is

Fresh Pokeroot (*prytolacca americana*) with a fresh herb strength in the ratio of 1 to 5 and a grain alcohol content of 60% which is available from GHIA HERBS, Harvard, Mass.

The aconite is aconitum with a fresh herb strength in the ratio of 1 to 5, with a grain alcohol content of 50 to 60%.

The aconite is available from VITALITY WORKS, 126 Quincy N.E. Albuquerque, N.M. 87108.

The four components in liquid form are combined in the following ranges to provide in a twelve milliliter dose.

Echinechea Goldenseal Supreme in the range of a trace to 6 ml, Wild Ginseng Supreme in the range of a trace to 6 ml, the combination of gelsium, pokeroot and aconite in the range of $\frac{1}{4}$ to $1\frac{1}{2}$ ml, (the range for gelsemium being $\frac{1}{12}$ ml to $\frac{1}{2}$ ml, the range for pokeroot being $\frac{1}{12}$ ml to $\frac{1}{2}$ ml, and the range for aconite being 1/12 ml to 1/2 ml) and aloe vera juice in the range of 2 to 11 ml.

It has been found that a 12 ml dose given twice a day to mastitis infected cows in accordance with the following example provided excellent results, with a total treatment time of 3 to 5 days.

EXAMPLE

1/2 ml Echinechea Goldenseal Supreme
1/2 ml Wild Ginseng Supreme
1/2 ml combination of gelsemium, pokeroot and aconite
10 1/2 ml aloe vera juice The 12 ml dose is injected by an infusion tube directly into a teat, which is attached to the infected quarter of the udder, at least twice a day with a suggested treatment time that varies from 3 to 5 days, depending on the degree of severity of the mastitis and the cows' response. The cows were tested for bovine mastitis at the end of the treatment period and all were found to be clear from infection and no mastitis byproducts were found in the milk.

In the compositions described the Echinechea Goldenseal Supreme may be present in a range of greater than 0% to 50% by weight of the composition, the Wild Ginseng Supreme may be present in a range of greater than 0% to 50% by weight of the composition, the gelsemium may be present in a range of 1% to about 4% by weight of the composition, pokeroot may be present in a range of 1% to about 4% by weight of the composition, the aconite may be present in a range of 1% to about 4% by weight of the composition, the gelsemium, pokeroot, and aconite may be present in equal amounts, and the aloe vera juice may be present in a range of about 16% to about 92% by weight of the composition.

It will thus be seen that compositions for the treatment of bovine mastitis have been provided with which the objects of the invention are achieved.

We claim:

1. A composition for the treatment of bovine mastitis, comprising a Goldenseal composition
a Ginseng composition
gelsemium,
pokeroot
aconite, and
aloe vera juice.

2. The composition of claim 1, the Goldenseal composition being in a range of greater than 0% to 50% by weight of the composition.

3. The composition of claim 1, the Ginseng composition being in a range of greater than 0% to 50% by weight of the composition.

4. The composition of claim 1, the gelsemium being in a range of 1% to about 4% by weight of the composition.

5. The composition of claim 1, the pokeroot being in a range of 1% to about 4% by weight of the composition.

6. The composition of claim 1, the aconite being in a range of 1% to about 4% by weight of the composition.

7. The composition of claim 1, the gelsemium, pokeroot, and aconite being in equal amounts.

8. The composition of claim 1, the aloe vera juice being in a range of about 16% to about 92% by weight of the composition.

9. The composition of claim 1, the Goldenseal composition being in a range of greater than 0% to 50% by weight of the composition, the Ginseng composition being in a range of greater than 0% to 50% by weight of the composition, the gelsemium being in a range of 1% to about 4% by weight of the composition, the pokeroot being in a range of 1% to about 4% by weight of the composition, the aconite being in a range of 1% to about 4% by weight of the composition, the gelsemium, pokeroot, and aconite being in equal amounts, and the aloe vera juice being in a range of about 16% to about 92% by weight of the composition.

10. A composition for the treatment of bovine mastitis, consisting essentially of a Goldenseal composition,
a Ginseng composition,
gelsemium,
pokeroot
aconite, and
aloe vera juice.

11. A composition for the treatment of bovine mastitis by direct infusion into at least one quarter of an infected cow's udder, comprising a Goldenseal composition in a range of a trace amount to 6 ml, a Ginseng composition in a range of a trace amount to 6 ml, gelsemium in a range of 1/12 ml to 1/2 ml, pokeroot in a range of 1/12 ml to 1/2 ml, aconite in a range of 1/12 ml to 1/2 ml, and aloe vera juice in a range of 2 ml to 11 ml, the composition comprising a total of 12 ml.

12. A method of treating bovine mastitis in a cow, comprising the steps of providing a composition for the treatment of bovine mastitis, said composition comprising a Goldenseal composition, a Ginseng composition, gelsemium, pokeroot, aconite, and aloe vera juice, administering an effective dosage of the composition to the cow by infusing the composition into at least one quarter of an infected cow's udder, and continuing to administer additional effective amounts of the composition periodically throughout a treatment period.

13. The method of claim 12, the Goldenseal composition being in a range of greater than 0% to 50% by weight of the composition.

14. The method of claim 12, the Ginseng composition being in a range of greater than 0% to 50% by weight of the composition.

15. The method of claim 12, the gelsemium being in a range of 1% to about 4% by weight of the composition.

16. The method of claim 12, the pokeroot being in a range of 1% to about 4% by weight of the composition.

17. The method of claim 12, the aconite being in a range of 1% to about 4% by weight of the composition.

18. The method of claim 12, the gelsemium, pokeroot, and aconite being in equal amounts.

19. The method of claim 12, the aloe vera juice being in a range of about 16% to about 92% by weight of the composition.

20. The method of claim 12,
the treatment period comprising administering the composition at least twice a day for three to five days in a row.

21. The method of claim 12,
the composition comprising, a Goldenseal composition in a range of a trace amount to 6 ml,
Ginseng in a range of a trace amount to 6 ml,
gelsemium in a range of 1/12 ml to ½ ml,
pokeroot in a range of 1/12 ml to ½ ml,
aconite in a range of 1/12 ml to ½ ml, and
aloe vera juice in a range of 2 ml to 11 ml,
the composition comprising a total of 12 ml.

22. The method of claim 12,
the Goldenseal composition being in a range of greater than 0% to 50% by weight of the composition,
the Ginseng composition being in a range of greater than 0% to 50% by weight of the composition,
the gelsium being in a range of 1% to about 4% by weight of the composition,
the pokeroot being in a range of 1% to about 4% by weight of the composition,
the aconite being in a range of 1% to about 4% by weight of the composition,
the gelsemium, pokeroot, and aconite being in equal amounts,
the aloe vera juice being in a range of about 16% to about 92% by weight of the composition and,
the treatment period comprising administering the composition at least twice a day for three to five days in a row.

23. A method of treating bovine mastitis in a cow, comprising the steps of
providing a composition for the treatment of bovine mastitis said composition consisting essentially of a Goldenseal Ginseng composition, gelsemium, pokeroot, aconite, and aloe vera juice,
administering an effective dosage of the composition to the cow by infusing the composition into at least one quarter of an infected cow's udder, and
continuing to administer additional effective amounts of the composition periodically throughout a treatment period.

* * * * *